(12) United States Patent
Bleau

(10) Patent No.: US 7,625,349 B2
(45) Date of Patent: Dec. 1, 2009

(54) BIOMECHANICAL CUSTOM MADE FOOT ORTHOSIS AND METHOD FOR MAKING THE SAME

(76) Inventor: Daniel Bleau, 470 Notre-Dame, Suite 100, Repentigny, Quebec (CA) J6A 2T5

( * ) Notice: Subject to any disclaimer, the term of this patent is extended or adjusted under 35 U.S.C. 154(b) by 427 days.

(21) Appl. No.: 10/537,253

(22) PCT Filed: Dec. 16, 2002

(86) PCT No.: PCT/CA02/01927

§ 371 (c)(1), (2), (4) Date: Jun. 1, 2005

(87) PCT Pub. No.: WO2004/054398

PCT Pub. Date: Jul. 1, 2004

(65) Prior Publication Data

US 2006/0015050 A1    Jan. 19, 2006

(51) Int. Cl.
*A61F 5/00* (2006.01)
(52) U.S. Cl. .................. 602/8; 602/23; 602/27
(58) Field of Classification Search .............. 602/7–8, 602/23, 27; 36/43, 44; 128/882
See application file for complete search history.

(56) References Cited

U.S. PATENT DOCUMENTS

| | | | |
|---|---|---|---|
| 3,995,002 A | 11/1976 | Brown | |
| 4,338,734 A | 7/1982 | Schwartz | |
| 4,513,518 A * | 4/1985 | Jalbert et al. | 36/44 |
| 4,688,338 A | 8/1987 | Brown | |
| 4,756,096 A | 7/1988 | Meyer | |
| 4,868,945 A | 9/1989 | DeBettignies | |
| 5,003,708 A | 4/1991 | Daley | |
| 5,282,326 A | 2/1994 | Schroer | |
| 5,775,332 A * | 7/1998 | Goldman | 600/587 |
| 5,958,546 A * | 9/1999 | Mardix et al. | 428/71 |
| 6,042,759 A | 3/2000 | Marshall | |
| 6,173,511 B1 | 1/2001 | Perrault | |
| 6,195,917 B1 | 3/2001 | Dieckhaus | |
| 6,282,816 B1 | 9/2001 | Rosendahl | |
| 2002/0158358 A1 | 10/2002 | Franzene | |

FOREIGN PATENT DOCUMENTS

| | | |
|---|---|---|
| GB | 565070 A | 10/1944 |
| WO | WO97/24041 | 7/1997 |

* cited by examiner

*Primary Examiner*—Michael Brown
(74) *Attorney, Agent, or Firm*—Goudreau Gage Dubuc; Gonzalo Lavin

(57) ABSTRACT

A biomechanical custom made foot orthosis (10) and a method for making the same. The orthosis (10) has a thermoformed flexible top layer (12) made of a first moldable synthetic rubber material, and a thermoformed flexible reinforcement core layer (14) made of a. moldable core material that is molded onto the top layer, (12). The core layer (14) has a posterior end (16) aligned with a mid anterior plantar prominence (K) of a calcaneus bone (C), and an anterior end (18) aligned near metatarsal-phalangeal joints (J) of the foot. The orthosis (10) also has a thermoformed flexible bottom layer (20) made of a second moldable synthetic rubber material that is molded onto the top layer (12) and the core layer (14). The core layer (14) is more rigid than the top and bottom layers (12, 20). The orthosis (10) corrects anatomic biomechanical deficiencies of the foot and ensuing body deficiencies.

17 Claims, 5 Drawing Sheets

BIOMECHANICAL CUSTOM MADE FOOT ORTHOSIS AND METHOD FOR MAKING THE SAME

FIELD OF THE INVENTION

The present invention relates to a biomechanical custom made foot orthosis and a method for making the same, but more particularly, to a foot orthosis used for correcting anatomic biomechanical deficiencies of a person's foot and ensuing body deficiencies.

BACKGROUND OF THE INVENTION

There are many anatomic biomechanical deficiencies of a foot that can be identified by a foot specialist: flat feet, raised arch, Morton's neuroma, foot inversion, foot eversion, hammer toes, corns, calluses, heel pain, plantar fasciitis, heel spur syndrome, etc. Some of these deficiencies may be interrelated. For example, a raised arch may cause other problems such as corns, calluses or heel pains as walking pressure is not properly distributed as compared to a normal foot. Other problems such as hammer toes may be caused by the type of footwear that is used, such as high heels or very tight shoes. Furthermore, foot deficiencies may also cause problems or deficiencies in other parts of the body, particularly in the legs and the back of a person.

Foot orthosis or insoles are used to support a human foot in footwear, and have been known for quite some time in the field. However, none has proven satisfactory for adequately correcting the most common anatomic biomechanical deficiencies of the foot and ensuing body deficiencies.

Foot orthosis can generally be classified in two kinds. The first kind of foot orthosis is manufactured on a mass production scale. This kind of foot orthosis is not adapted to properly correct a person's biomechanical foot deficiencies because each person has different kinds of foot deficiencies. For example, U.S. Pat. No. 4,338,734 (SCHWARTZ) and U.S. Pat. No. 6,282,816 (ROSENDAHL) disclose different kinds of foot orthosis or insoles that are made on a mass production basis.

Also known in the art, there is U.S. Pat. No. 6,173,511 and international patent publication No. WO 97/24041 (PERRAULT) both of which disclose a foot orthosis formed of a monolithic shell made of a semi-rigid, resilient plastic substance characterized in that it has a rear part provided with a pair of horns that curve around a large ovoid notch. Although the US patent claims that the foot orthosis can compensate for podiatric deficiencies, it has not proven satisfactory in terms of patient comfort and actual compensation for the deficiencies due to its general design and choice of manufacturing materials. Indeed, because such orthosis is made of a hard plastic extending from the back of the heel up to the toes, it does not allow making compensations or corrections such as, for example, heel corrections, metatarsal corrections, inversion and eversion corrections, etc.

U.S. Pat. No. 3,995,002 (BROWN); U.S. Pat. No. 4,513,518 (JALBERT); U.S. Pat. No. 4,688,338 (BROWN); U.S. Pat. No. 4,756,096 (MEYER); U.S. Pat. No. 4,868,945 (DE-BETTIGNIES); U.S. Pat. No. 5,003,708 (DALEY); U.S. Pat. No. 5,282,326 (SCHROER); U.S. Pat. No. 5,958,546 (MARDIX) and U.S. Pat. No. 6,195,917 (DIECKHAUS) disclose different kinds of foot orthosis or insoles, some of which are actually custom made. However, none of the foot orthosis or insoles disclosed can be used with satisfactory results to correct for anatomic biomechanical deficiencies of a person's foot.

SUMMARY OF THE INVENTION

According to the present invention there is provided a method for making a custom made foot orthosis for engagement inside a footwear and for conformingly fitting against a bottom surface of a foot of a person for correcting anatomic biomechanical deficiencies of the foot and ensuing body deficiencies of the person, said method comprising the steps of:
  a) producing a corrective positive mold of the bottom surface of the foot based on a specialist patient assessment and clinical measurement deficiencies of the foot to correct for the anatomic biomechanical deficiencies of the foot;
  b) thermoforming a first strip of moldable synthetic rubber material onto the corrective positive mold to produce a thermoformed flexible top layer sized for conformingly fitting against the bottom surface of the foot;
  c) thermoforming a moldable core strip onto the top layer to produce a thermoformed flexible reinforcement core layer sized for having a posterior end in alignment with a mid anterior plantar prominence of a calcaneus bone of the foot, and an anterior end in near alignment with metatarsalphalangeal joints defined between metatarsal bones and phalange bones of the foot;
  d) thermoforming a second strip of moldable synthetic rubber material onto the top layer and the core layer to produce a thermoformed flexible bottom layer, the core layer being more rigid than the top and bottom layers; and
  e) grinding the top and bottom layers to further correct for the anatomic biomechanical deficiencies of the foot;

thereby, when the foot orthosis is used by the person, the top and bottom layers cushion walking impacts on a calcaneus spine of the calcaneus bone of the foot, while the core layer transmits the walking impacts to a foot surface extending from the mid anterior plantar prominence of the calcaneus bone of the foot to near the metatarsalphalangeal joints.

According to the present invention, there is also provided a custom made foot orthosis for engagement inside a footwear and for conformingly fitting against a bottom surface of a foot of a person for correcting anatomic biomechanical deficiencies of the foot and ensuing body deficiencies of the person, said foot orthosis comprising:
  a thermoformed flexible top layer made of a first moldable synthetic rubber material, the top layer having a shape for conformingly fitting against the bottom surface of the foot;
  a thermoformed flexible core layer made of a moldable core material that is molded onto the top layer, the core layer having a posterior end aligned with a mid anterior plantar prominence of a calcaneus bone of the foot, and an anterior end aligned near metatarsalphalangeal joints defined between metatarsal bones and phalange bones of the foot; and
  a thermoformed flexible bottom layer made of a second moldable synthetic rubber material that is molded onto the top layer and the core layer, the core layer being more rigid than the top and bottom layers;

whereby, when the foot orthosis is used by the person, the top and bottom layers cushion walking impacts on a calcaneus spine of the calcaneus bone of the foot, while the core layer transmits the walking impacts to a foot surface extending from the mid anterior plantar prominence of the calcaneus bone of the foot to near the metatarsalphalangeal joints.

One advantage of the foot orthosis according to the present invention is that it can be designed to improve the biomechanical posture of the foot of a person and consequently the person's entire body posture. As the foot orthosis corrects for the biomechanical deficiencies of the person's foot, it can also reduce the pain associated with such deficiencies. In particular, in the case of a raised arch for example, the foot orthosis provides the necessary support while relaxing the muscles, and reducing stresses on ligaments and articulations. Thereby, the foot arch is lowered down to a normal anatomical scale. Furthermore, proper angular corrections to the heel, the metatarsal joints and the arch portion may easily be provided for with the present foot orthosis.

A second advantage of the foot orthosis is that its front, arched, and back portions are flexed in conformity with the foot flexure during walking.

A third advantage of the foot orthosis according to the present invention is that it is flexible enough to adapt itself to the height of the footwear's heel.

A fourth advantage of the foot orthosis according to the present invention is that it can be designed to relieve pressure where needed and may permit healing of foot problems such as heel spur syndrome, plantar faciitis, metatarsal pain, etc.

Other advantages of the foot orthosis according to the present invention is that it is very resistant to wear, it offers good aesthetics, it provides good aeration to the foot, it is waterproof, it does not smell and does not stain. It can be easily washed without worrying of causing damage to it because its external layers are made of synthetic rubber material.

The invention, its use and its advantages will be better understood upon reading of the following non-restrictive description of preferred embodiments thereof, made with reference to the accompanying drawings in which similar reference characters are used to refer to similar elements.

DETAILED DESCRIPTION OF THE INVENTION

Figure 1:
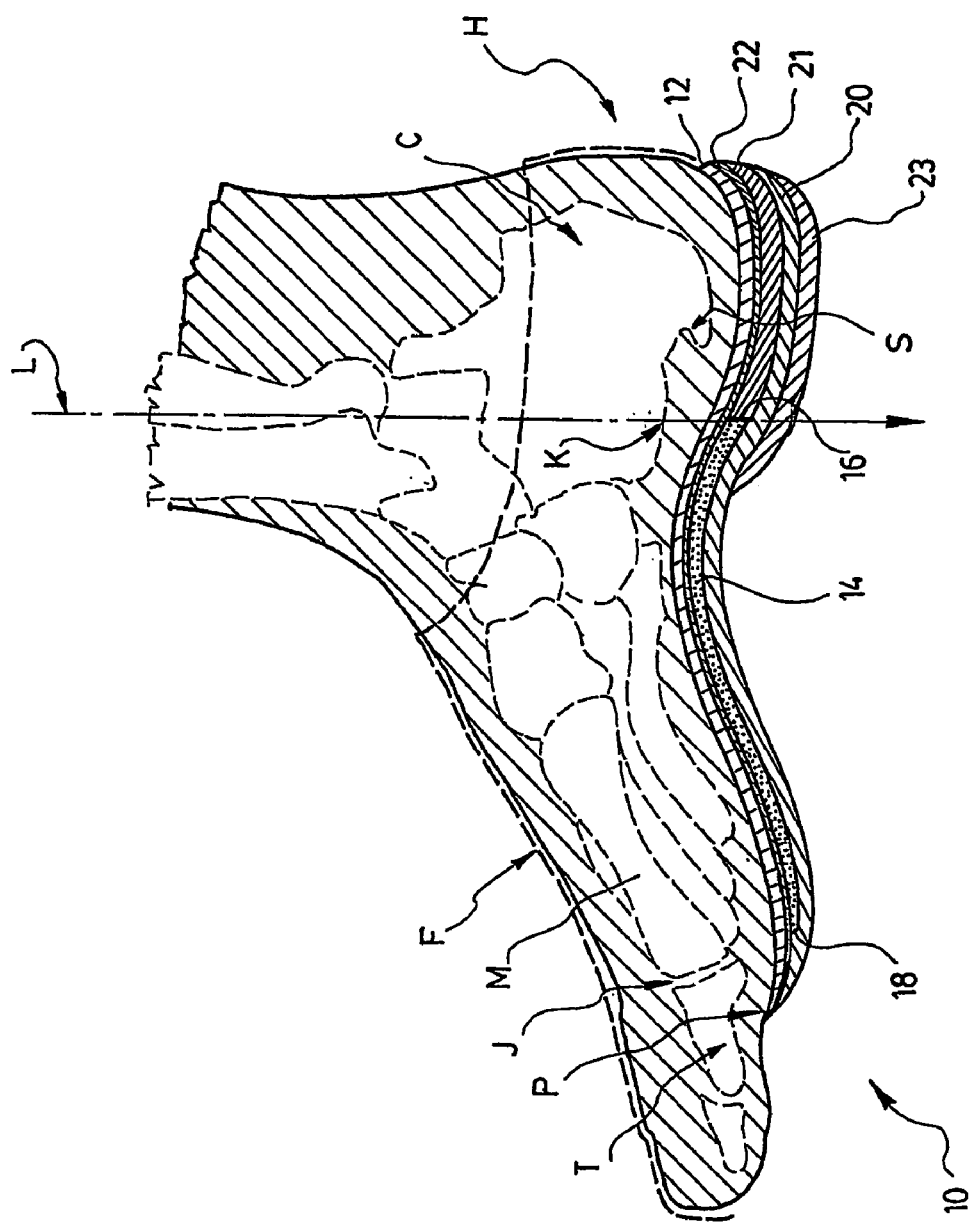
FIG. 1 is a side section view along lines I-I of FIG. 2 showing a right foot of a person inserted in a footwear and a biomechanical custom made foot orthosis according to a preferred embodiment of the present invention.
Figure 2:
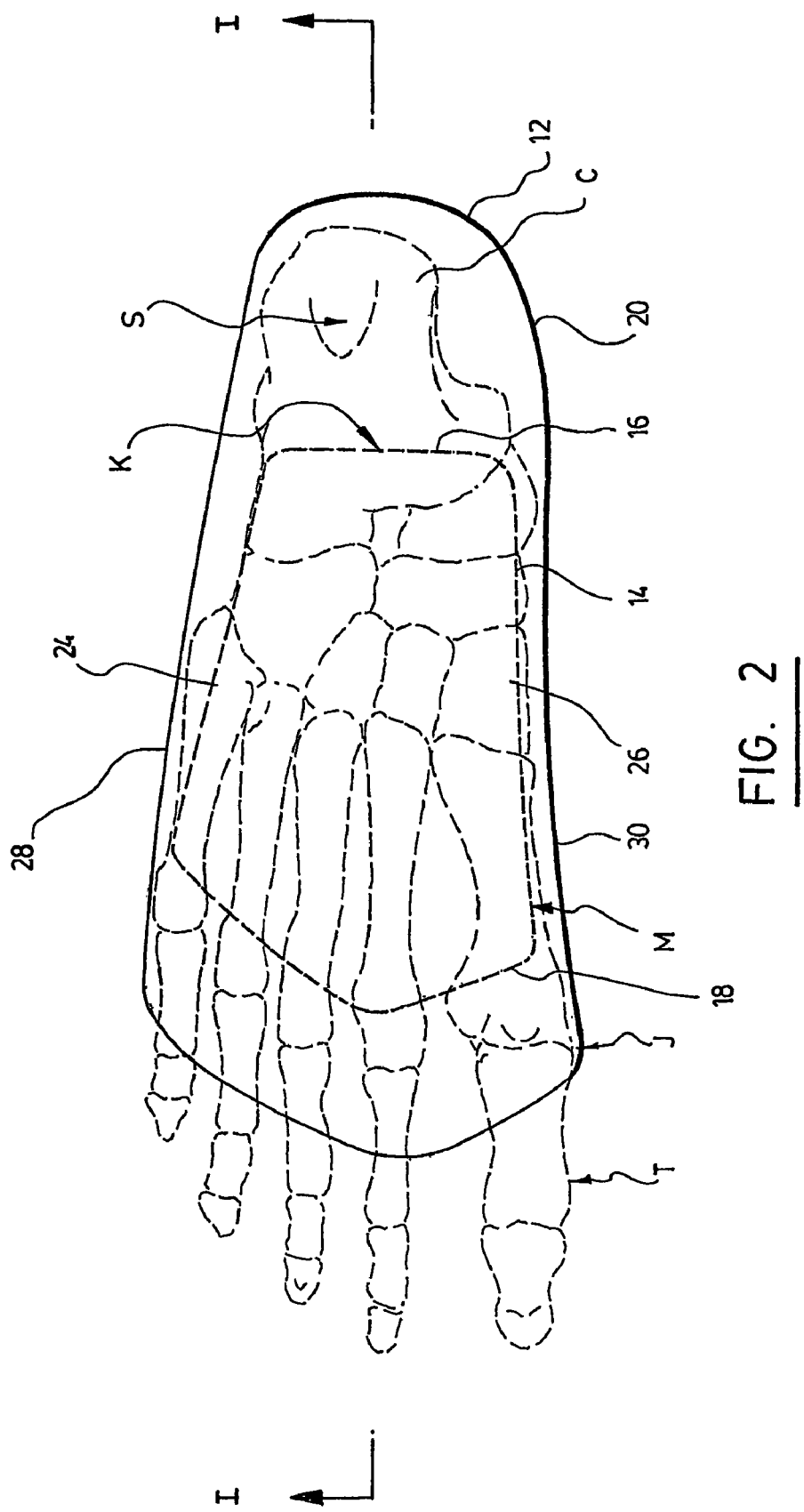
FIG. 2 is a bottom plan view showing the foot orthosis positioned under the foot of a person according to a preferred embodiment of the present invention.
Figure 3:
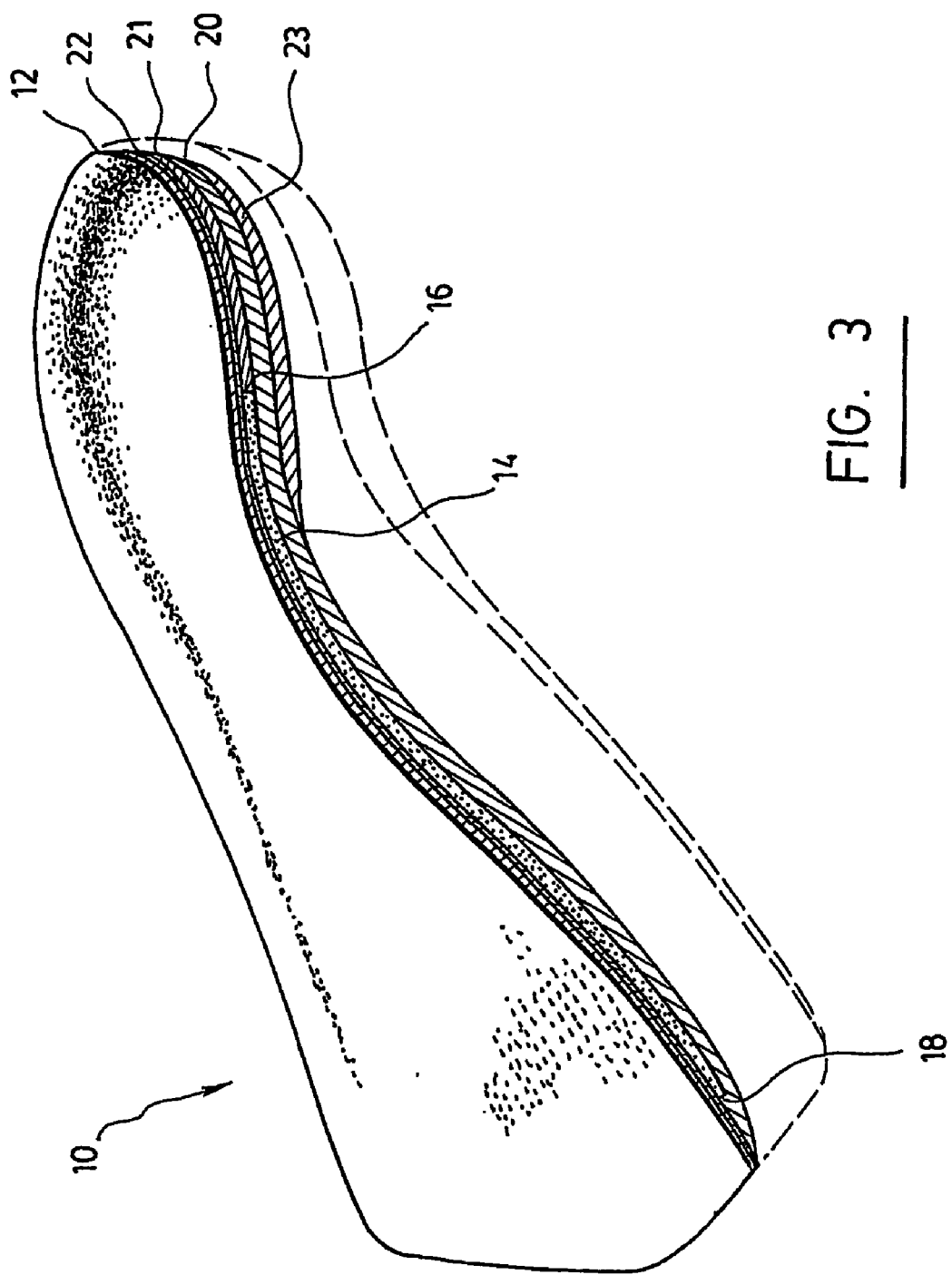
FIG. 3 is a perspective partly in section view of the foot orthosis according to a preferred embodiment of the present invention.

Referring to FIGS. 1 to 3, there is shown a preferred embodiment of a custom made foot orthosis 10 according to the present invention. As best illustrated in FIG. 1, the foot orthosis 10 is inserted inside a footwear F and conformingly fits against a bottom surface P of a foot of a person. The foot orthosis 10 is used to correct anatomic biomechanical deficiencies of the foot and ensuing body deficiencies, if any. As mentioned above, typical anatomic biomechanical deficiencies of the foot may include flat feet, raised arch, Morton's neuroma, foot inversion, foot eversion, hammer toes, corns, calluses, heel pain, plantar fasciitis, heel spur syndrome, etc. These foot deficiencies may also cause body deficiencies, such as leg or back problems.

The foot orthosis 10 has a thermoformed flexible top layer 12 made of a first moldable synthetic rubber material. The top layer 12 has a shape for conformingly fitting against the bottom surface of the foot P. The foot orthosis 10 also has a thermoformed flexible reinforcement core layer 14 made of a moldable core material that is molded onto the top layer 12. The core layer 14 has a posterior end 16 aligned with a mid anterior plantar prominence K of a calcaneus bone C of the foot, and an anterior end 18 aligned near metatarsalphalangeal joints J defined between metatarsal bones M and phalange bones T of the foot. The foot orthosis 10 also has a thermoformed flexible bottom layer 20 made of a second moldable synthetic rubber material that is molded onto the top layer 12 and the core layer 14. The core layer 14 is more rigid than the top layer 12 and bottom layer 20.

In use, when the orthosis 10 is inserted in person's footwear F, the top and bottom layers 12, 20 cushion walking impacts on a calcaneus spine S of the calcaneus bone C of the foot, while the core layer 14 transmits the walking impacts to a foot surface extending from the mid anterior plantar prominence K of the calcaneus bone C of the foot to near the metatarsalphalangeal joints J.

The location of the posterior end 16 of the core layer 14 is adapted to coincide with a vertical axis L passing through the anterior plantar prominence K of the calcaneus bone C, the talus, the tibia and fibula bones of the leg. As persons skilled in the art will understand, there can be some variations in the exact location of the posterior end 16 of the reinforcement core layer 14. It is important that the posterior end 16 not be aligned with the calcaneus spine S of the foot as this would transmit too much walking stress to a portion of the foot that is more vulnerable to such stress.

In test results, the best position for the location of the posterior end 16 of the reinforcement core layer 14 is the one illustrated in FIGS. 1 and 2, that is in the middle of the anterior plantar prominence K of the calcaneus bone C. However, it is possible that the posterior end 16 be closer to the calcaneus spine S without actually being aligned with it. Similarly, the posterior end 16 can be aligned closer to the anterior end of the calcaneus bone C. For the anterior end 18 of the core layer 14 there can also be some latitude as to its exact location. Thus, the anterior end 18 may be preferably aligned before the metatarsalphalangeal joints (J). It should be noted that in some rare cases the anterior end (18) may be aligned further after the metatarsalphalangeal joints (J).

Referring to FIG. 2, there is shown a more detailed view of the edges of the core layer 14, top and bottom layers 12, 20 and also the foot bones, as seen from below. Preferably, the side edges 24, 26 of the core layer 14 are spaced by about a quarter of an inch from the side edges 28, 30 of the top and bottom layers 12, 20. The side edges 24, 26 of the core layer 14 may also be flush with the side edges 28, 30 of the top and bottom layer 12, 20 depending on the particular foot deficiency.

Preferably, the foot orthosis 10 further has a thermoformed heel cushion layer 21 made of moldable synthetic rubber material that is molded onto the top layer 12 in alignment with a heel H of the foot extending from the mid anterior plantar prominence K of the calcaneus bone C of the foot to a back of the heel H. This heel strip of moldable synthetic rubber material is typically thicker and has a lower density than the first and second strips of synthetic rubber materials. In qualitative terms, the cushion layer 21 is softer than the top and bottom layers 12, 20. The cushion layer 21 is typically used for patients suffering from heel pain. It also permits alignment corrections of the foot. In other words, problems such as varus and valgus deficiencies can be corrected by choosing proper angles of the finalized orthosis. Indeed, the finalized orthosis has different cross section thickness and angular corrections depending on the patient's particular deficiencies.

Preferably, the foot orthosis 10 further includes a thermoformed additional layer 22 mounted onto the top layer 12. This additional layer 22 is typically thinner than the other layers 12, 20, 21. It has a typical thickness of about two millimeters and covers the entire length of the foot orthosis 10. The additional layer 22 provides extra cushioning to the foot and may be as soft as the cushion layer 21.

The foot orthosis 10 may also further include a thermoformed heel angular correction layer 23 made of moldable synthetic rubber material that is molded on a back of the bottom layer 20. This correction layer 23 may be used to adjust the height of the foot orthosis 10 as well as to correct for angular problems such as valgus and varus deficiencies. The correction layer 23 may be typically harder than the top and bottom layers 12, 20.

Preferably, the moldable synthetic rubber materials from which the thermoformed layers 12, 20, 21, 22, 23 are made is a mixture of ethylene, vinyl and acetate (EVA) material. The moldable synthetic material may also be selected from the Nickleplast™ family. Other suitable materials may include elastomers such as TPR (styrene based, Felprene™), TPU (urethane based), TPO (polypropylene base), metaloces, Esprenes™, and flexible PVC.

EVA materials have offered good performances in test results. Indeed, these materials have averaged better than other material, such as leather, moldable cork, or Dermaplast™. The resulting foot orthosis 10 offers very good resistance, flexibility, cushioning, thinness, memory capacity, hygiene and aesthetics. These materials also offer the possibility of modifying the orthosis 10 after it has been made and used by the patient.

The EVA sheets of material come in different kinds of hardness and thickness. The hardness can be qualitatively defined as: soft, medium and hard. Typically the top and bottom layers 12, 20 are medium or hard. The additional layer 21 and heel layer 22 are typically soft. The correction layer 23 is typically selected to be hard. The particular hardness and thickness of the synthetic rubber material is selected depending on the particular needs of the patient.

Preferably, the moldable core material is made of a prepreg material. It can also be made of plastic. The prepreg material forms a matrix which is a mixture of a resin and a composite material. The resin may be selected from a wide group including: polyesters, epoxies, phenolics, acrylics, polystyrenes, Nylon™, polyamides, polypropylenes, polyethylenes and Kydex™. The composite material may be selected from a wide group including: carbon fibers, Kevlar™ fibers, aramid fibers, polymer fibers, bore fibers, glass fibers or a mixture of carbon fibers, polyethylene fibers, polypropylene fibers and aramid fibers. The particular rigidity of the core material is selected depending on the particular needs of the patient as it will be apparent to those skilled in the art.

For example, in the case of flat feet, the core material is less flexible to provide better support for the arch. In the case of a raised arch, the core material is more flexible to allow the arch to be lowered toward the ground. In case of inversion or eversion of the foot, all the materials must be properly selected.

A preferred method for making a foot orthosis 10 according to the present invention begins by having a foot specialist examine the feet of a person. The foot specialist can determine one or several anatomic biomechanical deficiencies that affect the patient's foot or feet.

For example, the foot specialist may use a podoscope that provides a visual image of the pressure distribution over foot surface (P) as the person is standing. The podoscope consists of a box with a glass top. The glass top is illuminated on each side by fluorescent lights. A mirror is positioned below the glass to provide a view of the plantar surface of the foot.

Other more sophisticated approaches, such as computer imaging of the foot, or a pressure plate connected to a computer or a laser scanner to obtain the shape of the foot may be used to assist the specialist in identifying the biomechanical deficiencies of the foot.

Figure 4:
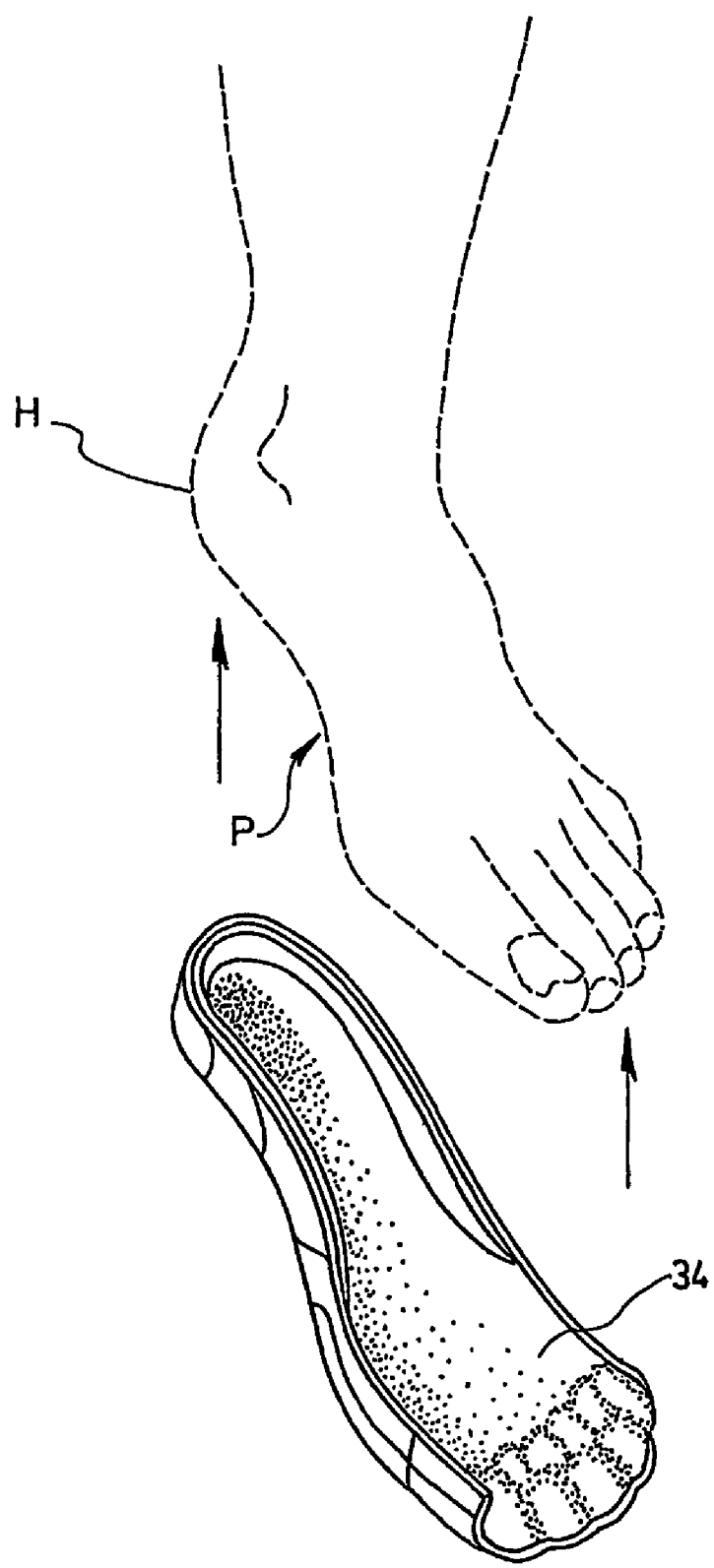
FIG. 4 is a perspective view of a foot suffering from a raised arch and a negative plaster mold of the foot that is produced according to a preferred embodiment of the present invention.
Figure 5:
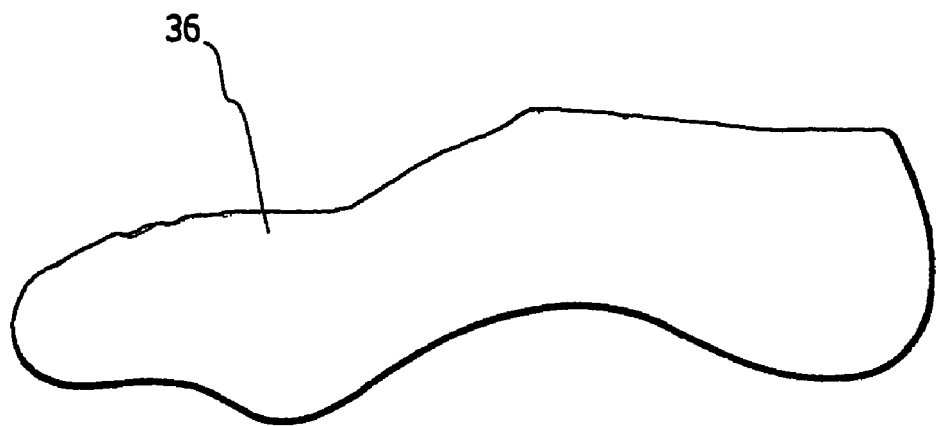
FIG. 5 is a side view of a positive plaster mold made from the negative plaster mold shown in FIG. 4 according to a preferred embodiment of the present invention.
Figure 6:
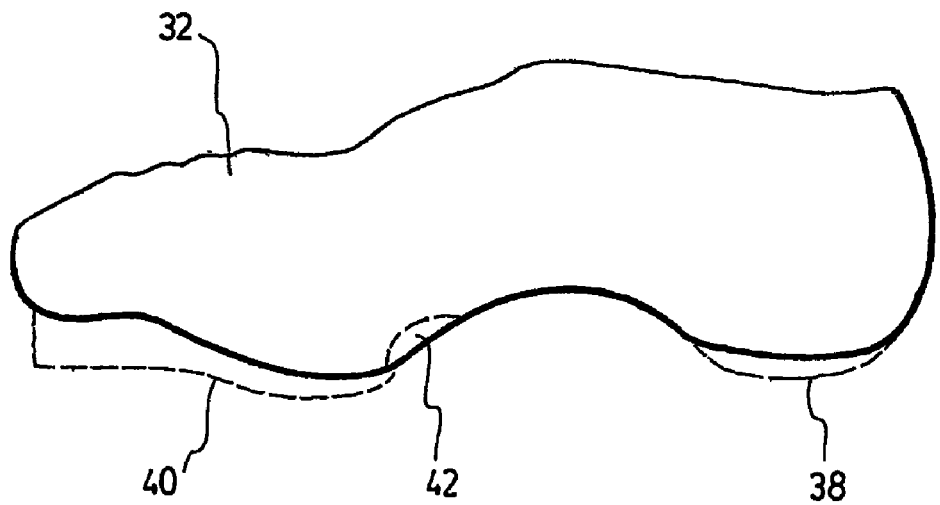
FIG. 6 is a side view of a corrective positive plaster mold made from the positive plaster mold shown in FIG. 5 according to a preferred embodiment of the present invention.

Referring now also to FIGS. 4 to 6, a basic method for making the custom made orthosis 10 according to the invention basically consists of the following steps:

a) producing a corrective positive mold 32 of the bottom surface P of the foot based on a specialist patient assessment and clinical measurement deficiencies of the foot to correct for the anatomic biomechanical deficiencies of the foot;

b) thermoforming a first strip of moldable synthetic rubber material onto the corrective positive mold 32 to produce a thermoformed flexible top layer 12 sized for conformingly fitting against the bottom surface P of the foot;

c) thermoforming a moldable core strip onto the top layer 12 to produce a thermoformed flexible core layer 14 sized for having a posterior end 16 in alignment with a mid anterior plantar prominence K of a calcaneus bone C of the foot, and an anterior end 18 in near alignment with metatarsalphalangeal joints J defined between metatarsal bones M and phalange bones T of the foot;

d) thermoforming a second strip of moldable synthetic rubber material onto the top layer 12 and the core layer 14 to produce a thermoformed flexible bottom layer 20, the thermoformed core layer 14 being more rigid than the top and bottom layers 12, 20; and e) grinding the top and bottom layers 12, 20 to further correct for the anatomic biomechanical deficiencies of the foot;

thereby, when the orthosis 10 is used by the person, the top and bottom layers 12, 20 cushion walking impacts on a calcaneus spine S of the calcaneus bone C of the foot, while the core layer 14 transmits the walking impacts to a foot surface extending from the mid anterior plantar prominence K of the calcaneus bone C of the foot to near the metatarsalphalangeal joints J.

Preferably, the first and second strips may be cut from a sheet of EVA material of about six millimeters. Of course other thickness may be chosen depending on the patient's needs.

The grinding step (e) may be carried out with any suitable grinding machine that is able to grind away the thermoformed synthetic rubber material as it will be understood by those skilled in the art. The grinding step also assists in performing alignment corrections of the foot, which may be affected by varus and valgus deficiencies. As mentioned above, the finalized foot orthosis 10 has different cross section thickness and angular corrections depending on the patient's particular deficiencies.

In the above method, step a) may also include the steps of:

i) producing a negative mold 34 of the bottom surface P of the foot, as shown for example in FIG. 4;

ii) modifying the negative mold 34 to produce a corrected negative mold based on the specialist patient assessment and clinical measurement deficiencies of the foot to correct for the anatomic biomechanical deficiencies of the foot;

iii) producing a positive mold 36 from the corrected negative mold, as shown for example in FIG. 5; and iv) modifying the positive mold 36 to produce the corrective positive mold 32 based on the specialist patient assessment and clinical measurement deficiencies of the foot to further relieve or add pressure so as to further correct for the anatomic biomechanical deficiencies of the foot, as shown for example in FIG. 6.

It should be noted that the corrected negative mold that is produced at step ii) is made by a foot specialist according to the assessment of the patient's foot. In other words, the specialist determines the required alignments, pressure addition or pressure relief based on a clinical measurement of the deficiencies of the foot and body.

It should also be noted that the above molds 32, 34 and 36 are preferably made of plaster material, but any other suitable material may be selected to obtain the same results.

Furthermore, although the foot that is illustrated in FIG. 4 suffers from a raised arch, the above method may be used in a similar way for other types of deficiencies as it will be understood by those skilled in the art. In the case of the foot shown in FIG. 4, step iv) of the above method of forming the corrective positive mold 32 involves adding or removing plaster material as shown in FIG. 6. For example, as shown in dotted lines, the positive mold 36 is modified to produce the corrective mold 32 by adding plaster material in a back portion 38 and in a front portion 40, while plaster material is removed in a middle portion 42. In this way, the resulting foot orthosis 10 will relive or add pressure to the foot, thereby providing the appropriate pressure to all the parts of the foot in order to correct for its deficiency. thus, the foot orthosis 10 provides the necessary support while relaxing the muscle, ligament and articulation stresses so that the foot arch is lowered down to a normal anatomical scale.

Alternatively, the above step a) may be replaced by following the steps of:

i) producing a three dimensional computer representation of the bottom surface P of the foot;

ii) modifying the three dimensional computer representation of the foot to produce a corrected three dimensional computer based on the specialist patient assessment and clinical measurement deficiencies of the foot to correct for the anatomic biomechanical deficiencies of the foot; and iii) producing the corrective positive mold 32 from the corrected negative three dimensional computer representation.

As those skilled in the art will understand, the corrective positive mold 32 may thus be fabricated by using a computer where all the corrections are carried out. The computer may then instruct a machine to actually manufactures the mold 32. Preferably, steps b), c) and d) comprise the steps of:

i) heating the first strip in an oven, at about 300 to 400 degrees Fahrenheit, to produce a first heated strip;

ii) mounting the first heated strip onto the positive mold 32;

iii) applying a vacuum to the heated strip that is mounted onto the corrective positive mold 32 by means of a vacuum device to produce the thermoformed flexible top layer 12;

iv) applying a glue onto the top layer 12 that is mounted on the corrective positive mold 32;

v) cutting the core strip from a sheet made of a reinforcement core material;

vi) grinding the core strip to produce a core strip with smother edges;

vii) applying a glue onto a face of the core strip;

viii) heating the core strip in the oven to produce a heated core strip;

ix) mounting the heated core strip onto the top layer 12;

x) applying a glue onto a face of the second strip of moldable synthetic rubber material;

xi) heating the second strip of moldable synthetic rubber material in the oven to produce a second heated strip;

xii) mounting the second heated strip onto the top layer 12 and the heated core strip; and xiii) applying a vacuum to the heated core strip and second heated strip that are mounted onto the top layer 12 by means of the vacuum device to produce respectively the thermoformed core layer 14 and thermoformed bottom layer 20.

The vacuum device preferably includes a rubber sheet that is pressed against the layers that are mounted on the corrective positive mold 32 by means of a vacuum. Of course, other mechanisms may be used to mold the layers. For example, instead of using the vacuum device, the layers may be strapped together with a band that provides the appropriate pressure. The band may be an elastic band and may be also used in combination with the vacuum device.

Preferably, the method also involves the step of thermoforming a heel strip of moldable synthetic rubber material onto the top layer 12 to produce the thermoformed heel cushion layer 21 as discussed above. The method may also involve thermoforming an additional strip of moldable synthetic rubber material onto the top layer to produce the thermoformed additional layer 22 as discussed above.

The method may be further modified so that step d) further comprises the step of thermoforming an additional heel strip of moldable synthetic rubber material onto the second strip of moldable material to produce the thermoformed heel angular correction layer 23. As mentioned above, the heel angular correction layer 23 is particularly useful for correcting varus and valgus deficiencies.

An advantage of the foot orthosis 10 is that it can be further corrected after it has been fabricated and been used by the patient. Thus, the above method may also include the step of gluing a corrective strip of synthetic rubber material onto the foot orthosis 10 for further correcting for the anatomic biomechanical deficiencies of the foot. Indeed, it is possible to have the foot orthosis 10 gun heated to further correct it once it has been used for some time by the patient.

Clinical trials over a significant time period have provided very good results. In some patients, there has been a notable improvement of the biomechanical deficiencies of their feet, legs, back, a reduction in body pain and pressure in the foot and upward articulations. These results have been confirmed by using the podoscope, a pressure plate analyzed by a computer, and the surrounding laser scanner.

The orthosis according to the present invention improves the biomechanical posture and angles of the foot, legs and back, at the saggital, coronal and transversal planes, and if needed, the elevation of the legs (e.g. for correcting the back angle in a scoliosis). Consequently, it improves the entire body posture at the mid-saggital, mid-coronal, and mid-transverse planes (varus, valgus, dorsification, plantar flexion, extension, hyperextension, adduction, inversion, eversion, circumduction, supination, pronation, flexor) and helps the patient's clinical deficiencies of the body's center of gravity, while reducing the pain during the adaptation period when the orthosis is first used.

The orthosis according to the present invention may be used in any type of footwear and offers better aesthetics, better hygiene, greater flexibility, greater resistance, good aeration, impermeability and does not stain and does not smell.

The orthosis according to the present invention corrects for biomechanical deficiencies of the foot at the heel level (median and lateral), at the arch level (median and lateral), at the metatarsal level, at the post-metatarsal level, at the toe contact level and upward legs and back.

Although a preferred embodiment of the present invention has been described in detail herein and illustrated in the accompanying drawings, it is to be understood that the invention is not limited to this precise embodiment and that various changes and modifications may be effected therein without departing from the scope or spirit of the present invention.

The invention claimed is:

1. A method for making a custom made foot orthosis (10) for engagement inside a footwear (F) and for conformingly fitting against a bottom surface (P) of a foot of a person for correcting anatomic biomechanical deficiencies of the foot and ensuing body deficiencies of the person, said method comprising the steps of:
   a) producing a corrective positive mold (32) of the bottom surface (P) of the foot based on a specialist patient assessment and clinical measurement deficiencies of the foot to correct for the anatomic biomechanical deficiencies of the foot;
   b) thermoforming a first strip of moldable synthetic rubber material onto the corrective positive mold (32) to produce a thermoformed flexible top layer (12) sized for conformingly fitting against the bottom surface (P) of the foot;
   c) thermoforming a moldable core strip onto the top layer (12) to produce a thermoformed flexible reinforcement core layer (14) sized for having a posterior end (16) in alignment with a mid anterior plantar prominence (K) of a calcaneus bone (C) of the foot, and an anterior end (18) in near alignment with metatarsalphalangeal joints (J) defined between metatarsal bones (M) and phalange bones (T) of the foot;
   d) thermoforming a second strip of moldable synthetic rubber material onto the top layer (12) and the core layer (14) to produce a thermoformed flexible bottom layer (20), the core layer (14) being more rigid than the top and bottom layers (12, 20); and
   e) grinding the top and bottom layers (12, 20) to further correct for the anatomic biomechanical deficiencies of the foot; thereby, when the foot orthosis (10) is used by the person, the top and bottom layers (12, 20) cushion walking impacts on a calcaneus spine (S) of the calcaneus bone (C) of the foot, while the core layer (14) transmits the walking impacts to a foot surface extending from the mid anterior plantar prominence (K) of the calcaneus bone (C) of the foot to near the metatarsalphalangeal joints (J).

2. The method for making the custom made foot orthosis (10) according to claim 1, wherein step a) comprises the steps of:
   i) producing a negative mold (34) of the bottom surface (P) of the foot;
   ii) modifying the negative mold (34) to produce a corrected negative mold based on the specialist patient assessment and clinical measurement deficiencies of the foot to correct for the anatomic biomechanical deficiencies of the foot;
   iii) producing a positive mold (36) from the corrected negative mold; and
   iv) modifying the positive mold (36) to produce the corrective positive mold (32) based on the specialist patient assessment and clinical measurement deficiencies of the foot to further relieve or add pressure to the foot.

3. The method for making the custom made foot orthosis (10) according to claim 1, wherein step a) comprises the steps of:
   i) producing a three dimensional computer representation of the bottom surface (P) of the foot;
   ii) modifying the three dimensional computer representation of the bottom surface (P) of the foot to produce a corrected three dimensional computer representation based on the specialist patient assessment and clinical measurement deficiencies of the foot to correct for the anatomic biomechanical deficiencies of the foot; and
   iii) producing the corrective positive mold (32) from the corrected negative three dimensional computer representation.

4. The method for making the custom made foot orthosis according to claim 1, wherein steps b), c) and d) comprise the steps of:
   i) heating the first strip to produce a first heated strip;
   ii) mounting the first heated strip onto the corrective positive mold (32);
   iii) molding the first heated strip that is mounted onto the corrective positive mold (32) to produce the thermoformed flexible top layer (12);
   iv) applying a glue onto the top layer (12) that is mounted on the corrective positive mold (32);
   v) applying a glue onto a face of the core strip;
   vi) heating the core strip to produce a heated core strip;
   vii) mounting the heated core strip onto the top layer (12);
   viii) applying a glue onto a face of the second strip;
   ix) heating the second strip to produce a second heated strip;
   x) mounting the second heated strip onto the top layer (12) and the heated core strip; and
   xi) molding the heated core strip and second heated strip that are mounted onto the top layer (12) to produce respectively the thermoformed core layer (14) and thermoformed bottom layer (20).

5. The method for making the custom made foot orthosis (10) according to claim 1, wherein the step iii) of molding includes the step of applying a vacuum to the heated strip that is mounted onto the corrective positive mold (32) by means of a vacuum device to produce the thermoformed flexible top layer (12), and the step xi) includes the step of applying a vacuum to the heated core strip and second heated strip that are mounted onto the top layer (12) by means of the vacuum device to produce respectively the thermoformed core layer (14) and thermoformed bottom layer (20).

6. The method for making the custom made foot orthosis (10) according to claim 1, wherein the moldable core strip is made of a material selected from the group including: a plastic and a prepreg.

7. The method for making the custom made foot orthosis according to claim 1, wherein the moldable synthetic rubber materials are made from a mixture of ethylene, vinyl and acetate.

8. The method for making the custom made foot orthosis according to claim 1, wherein step b) further comprises the step of thermoforming a heel strip of moldable synthetic rubber material onto the top layer to produce a thermoformed heel cushion layer (21) in alignment with a heel (H) of the foot extending from the mid anterior plantar prominence (K) of the calcaneus bone (C) of the foot to a back of the heel (H).

9. The method for making the custom made foot orthosis according to claim 8, wherein the heel strip of moldable synthetic rubber material is thicker and has a lower density than the first and second strips of synthetic rubber materials.

10. The method for making the custom made foot orthosis according to claim 1, wherein step b) further comprises the step of thermoforming an additional strip of moldable synthetic rubber material onto the top layer (12) to produce a thermoformed additional layer (22).

11. The method for making the custom made foot orthosis according to claim 10, wherein step b) further comprises the step of thermoforming a heel strip of moldable synthetic rubber material onto the additional layer (22) to produce a thermoformed heel cushion layer (21) in alignment with a heel (H) of the foot extending from the mid anterior plantar prominence (K) of the calcaneus bone (C) of the foot to a back of the heel (H).

12. The method for making the custom made foot orthosis according to claim 1, wherein step d) further comprises the step of thermoforming an additional heel strip of moldable synthetic rubber material onto the second strip of moldable material to produce a thermoformed heel angular correction layer (23).

13. The method for making the custom made foot orthosis according to claim 1, further comprising the steps of gun heating and gluing a corrective strip of synthetic rubber material onto the orthosis for further correcting for the anatomic biomechanical deficiencies of the foot.

14. A custom made foot orthosis (10) for engagement inside a footwear (F) and for conformingly fitting against a bottom surface (P) of a foot of a person for correcting anatomic biomechanical deficiencies of the foot and ensuing body deficiencies of the person, said foot orthosis (10) comprising:
   a thermoformed flexible top layer (12) made of a first moldable synthetic rubber material, the top layer (12) having a shape for conformingly fitting against the bottom surface (P) of the foot;
   a thermoformed flexible reinforcement core layer (14) made of a moldable core material that is molded onto the top layer (12), the core layer (14) having a posterior end (16) aligned with a mid anterior plantar prominence (K) of a calcaneus bone (C) of the foot, and an anterior end (18) aligned near metatarsalphalangeal joints (J) defined between metatarsal bones (M) and phalange bones (T) of the foot; and
   a thermoformed flexible bottom layer (20) made of a second moldable synthetic rubber material that is molded onto the top layer (12) and the core layer (14), the core layer (14) being more rigid than the top and bottom layers (12, 20); whereby, when the foot orthosis (10) is used by the person, the top and bottom layers (12, 20) cushion walking impacts on a calcaneus spine (S) of the calcaneus bone (C) of the foot, while the core layer (14) transmits the walking impacts to a foot surface extending from the mid anterior plantar prominence (K) of the calcaneus bone (C) of the foot to near the metatarsalphalangeal joints (J); wherein the foot orthosis further comprises a thermoformed heel cushion layer (21) made of moldable synthetic rubber material that is molded onto the top layer (12) in alignment with a heel (H) of the foot extending form the mid anterior plantar prominence (K) of the calcaneus bone (C) of the foot to a back of the heel (H), the heel strip of moldable synthetic rubber material being thicker and having a lower density than the first and second strips of synthetic rubber materials.

15. The custom made foot orthosis (10) according to claim 14, wherein the moldable core material is made of a plastic or a prepreg.

16. The custom made foot orthosis (10) according to claim 14, wherein the moldable synthetic rubber materials are made from a mixture of ethylene, vinyl and acetate.

17. A custom made foot orthosis (10) for engagement inside a footwear (F) and for conformingly fitting against a bottom surface (P) of a foot of a person for correcting anatomic biomechanical deficiencies of the foot and ensuing body deficiencies of the person, said foot orthosis (10) comprising:
   a thermoformed flexible top layer (12) made of a first moldable synthetic rubber material, the top layer (12) having a shape for conformingly fitting against the bottom surface (P) of the foot;
   a thermoformed flexible reinforcement core layer (14) made of a moldable core material that is molded onto the top layer (12), the core layer (14) having a posterior end (16) aligned with a mid anterior plantar prominence (K) of a calcaneus bone (C) of the foot, and an anterior end (18) aligned near metatarsalphalangeal joints (J) defined between metatarsal bones (M) and phalange bones (T) of the foot; and
   a thermoformed flexible bottom layer (20) made of a second moldable synthetic rubber material that is molded onto the top layer (12) and the core layer (14), the core layer (14) being more rigid than the top and bottom layers (12, 20); whereby, when the foot orthosis (10) is used by the person, the top and bottom layers (12, 20) cushion walking impacts on a calcaneus spine (S) of the calcaneus bone (C) of the foot, while the core layer (14) transmits the walking impacts to a foot surface extending from the mid anterior plantar prominence (K) of the calcaneus bone (C) of the foot to near the metatarsaiphalangeal joints (J), wherein the foot orthosis further comprises:
   a thermoformed additional layer (22) made of moldable synthetic rubber material that is molded onto the top layer (12);
   a thermoformed heel cushion layer (21) made of moldable synthetic rubber material that is molded onto the additional layer (22) in alignment with a heel (H) of the foot extending from the mid anterior plantar prominence (K) of the calcaneus bone (C) of the foot to a back of the heel (H); and
   a thermoformed heel angular correction layer (23) made of moldable synthetic rubber material that is molded on a back of the bottom layer (20).

* * * * *

UNITED STATES PATENT AND TRADEMARK OFFICE
CERTIFICATE OF CORRECTION

PATENT NO. : 7,625,349 B2  Page 1 of 1
APPLICATION NO. : 10/537253
DATED : December 1, 2009
INVENTOR(S) : Daniel Bleau It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1142 days.

Signed and Sealed this

Twenty-first Day of December, 2010

David J. Kappos
*Director of the United States Patent and Trademark Office*